United States Patent [19]

Kober et al.

[11] Patent Number: 5,034,049
[45] Date of Patent: Jul. 23, 1991

[54] THIOPHENE-2-CARBOXYLIC ACID DERIVATIVES, THEIR PREPARATION AND THEIR USE FOR CONTROLLING UNDESIRABLE PLANT GROWTH

[75] Inventors: Reiner Kober; Rainer Seele, both of Fussgoenheim; Hans-Juergen Neubauer, Muenster-Hiltrup; Thomas Saupe, Sandhausen; Bruno Wuerzer, Otterstadt; Norbert Meyer, Ladenburg; Karl-Otto Westphalen, Speyer, all of Fed. Rep. of Germany

[73] Assignee: BASF Aktiengesellschaft, Ludwigshafen, Fed. Rep. of Germany

[21] Appl. No.: 463,163

[22] Filed: Jan. 9, 1990

[30] Foreign Application Priority Data

Jan. 16, 1989 [DE] Fed. Rep. of Germany ....... 3901074

[51] Int. Cl.$^5$ .................. A01N 43/02; C07D 333/38
[52] U.S. Cl. ............................................. 71/90; 549/61; 549/62; 549/63; 549/64; 549/71; 549/72
[58] Field of Search ............... 549/71, 72, 61, 62, 549/63, 64; 71/90

[56] References Cited

U.S. PATENT DOCUMENTS 3,536,473 10/1970 Popoff et al.
4,565,812 1/1986 King .................................... 514/189
4,920,110 4/1990 Neubauer et al.

FOREIGN PATENT DOCUMENTS 3629584 3/1988 Fed. Rep. of Germany.

OTHER PUBLICATIONS

Chem. Abst., King, 105:43091j, (1986).
Chem. Abst., Substance Index, 1982-1986, 2-Thiophene carboxamide—,N-Methoxy.
Heterocyclic Compounds, Thiophene and its Derivatives, vol. 44, Part 1, N.Y., 1984, p. 1.
D. Pillon et al., Univ. Ther., 5, 32, (1970).

*Primary Examiner*—Alan Siegel
*Attorney, Agent, or Firm*—Keil & Weinkauf

[57] ABSTRACT

Thiophene-2-carboxylic acid derivatives of the general formula I

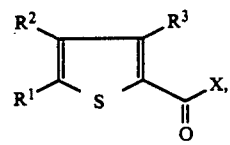

where
$R^1$ to $R^3$ are each hydrogen, halogen, branched or straight-chain $C_1$-$C_6$-alkyl, $C_1$-$C_8$-alkoxy, $C_1$-$C_6$-haloalkyl, $C_1$-$C_6$-haloalkoxy, nitro, cyano, unsubstituted phenyl or phenyl which is mono- to trisubstituted by $C_1$-$C_4$-alkyl, halogen, $C_1$-$C_5$-haloalkyl, $C_1$-$C_4$-alkoxy or $C_1$-$C_5$-haloalkoxy;
X is —$OR^4$ or —NH—$OR^5$,
$R^4$ being branched or straight-chain $C_3$-$C_{10}$-alkynylalkyl which is unsubstituted or substituted by halogen; and
$R^5$ being branched or straight-chain $C_1$-$C_5$-alkyl which is unsubstituted or substituted by halogen, or branched or straight-chain $C_3$-$C_{10}$-alkynylalkyl which is unsubstituted or substituted by halogen;
with the proviso that $R^4$ is not propargyl when $R^2$ and $R^3$ are both hydrogen or when $R^2$ is halogen or $R^3$ is chlorine, methyl or methoxy.

The compounds I are suitable for combating the growth of unwanted plants.

3 Claims, No Drawings

THIOPHENE-2-CARBOXYLIC ACID DERIVATIVES, THEIR PREPARATION AND THEIR USE FOR CONTROLLING UNDESIRABLE PLANT GROWTH

The present invention relates to novel herbicidal thiophene-2-carboxylic acid derivatives of the general formula I

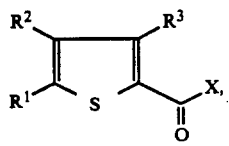

where
$R^1$ to $R^3$ are each hydrogen, halogen, branched or straight-chain $C_1$–$C_6$-alkyl, $C_1$–$C_8$-alkoxy, $C_1$–$C_6$-haloalkyl, $C_1$–$C_6$-haloalkoxy, nitro, cyano, or phenyl which is unsubstituted or monosubstituted to trisubstituted by $C_1$–$C_4$-alkyl, halogen, $C_1$–$C_5$-haloalkyl, $C_1$–$C_4$-alkoxy or $C_1$–$C_5$-haloalkoxy,
X is —$OR^4$ or —NH—$OR^5$,
$R^4$ is branched or straight-chain $C_1$–$C_{10}$-alkynylalkyl which may be unsubstituted or substituted by halogen and
$R^5$ is branched or straight-chain $C_1$–$C_5$-alkyl which is unsubstituted or branched or straight-chain $C_3$–$C_{10}$-alkynylalkyl which may be unsubstituted or substituted by halogen,
with the proviso that $R^4$ is not propargyl when $R^2$ and $R^3$ are each hydrogen or when $R^2$ is halogen or $R^3$ is chlorine, methyl or methoxy.

The present invention furthermore relates to a process for the preparation of thiophene-2-carboxylic acid derivatives I and their use for controlling undesirable plant growth. Chim. Ther. 5 (1970), 32 discloses amides of 3,4,5-trichlorothiophene-2-carboxylic acid for controlling parasites.

U.S. Pat. No. 3,536,473 describes halogenated thiophene-2-carboxylic acids and their salts, and derivatives, such as esters or amides which can be hydrolyzed to acids, as agents for regulating plant growth. DE-A-36 29 584 teaches that propargyl thiophene-2-carboxylates which may be substituted can be used as pesticides. This publication does not indicate other activity, for example herbicidal activity.

It is an object of the present invention to provide novel thiophene-2-carboxylic acid derivatives having good herbicidal activity. It is a further object of the present invention to find novel biological actions of conventional pesticides.

We have found that these objects are achieved by the thiophene-2-carboxylic acid derivatives of the general formula I which are defined at the outset.

In formula I,
$R^1$-$R^3$ are each preferably hydrogen;
halogen, such as fluorine, chlorine, bromine or iodine, in particular fluorine, chlorine or bromine;
$C_1$–$C_6$-alkyl, in particular $C_1$–$C_4$-alkyl, such as methyl, ethyl, isopropyl, n-propyl, n-butyl, isobutyl, sec-butyl or tert-butyl;
$C_1$–$C_8$-alkoxy, in particular $C_1$–$C_4$-alkoxy, such as methoxy, ethoxy, propyloxy, 1-methylethoxy, butoxy, 1-methylpropyloxy, 2-methylpropyloxy or 1,1-dimethylethoxy;
$C_1$–$C_6$-haloalkyl, in particular $C_1$–$C_4$-haloalkyl, such as fluoromethyl, difluoromethyl, trifluoromethyl, chlorodifluoromethyl, dichlorofluoromethyl, trichloromethyl, 1fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl;
$C_1$–$C_6$-haloalkoxy, in particular $C_1$–$C_4$-haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2trifluoroethoxy, 2-chloro-1,1,2-trifluoroethoxy or pentafluoroethoxy;
nitro, cyano;
phenyl which is unsubstituted or monosubstituted to trisubstituted, suitable substituents being $C_1$–$C_4$-alkyl, halogen, $C_1$–$C_5$-haloalkyl, $C_1$–$C_4$-alkoxy or $C_1$–$C_5$-haloalkoxy, for example as stated specifically for $R^1$ to $R^3$.

$R^1$, $R^2$ and $R^3$ are each particularly preferably hydrogen, fluorine, chlorine, bromine, iodine, methyl, ethyl, isopropyl, cyclopropyl, methoxy, ethoxy, isopropyloxy, chloromethyl, trifluoromethyl, trifluoromethoxy or phenyl which may be monosubstituted to trisubstituted by halogen or alkyl or substituted alkyl functions as stated above, for example 4-chlorophenyl, 3,5-dichlorophenyl, 3-trifluoromethylphenyl, 4-methoxyphenyl or 2-fluoro-4-chlorophenyl.

$R^4$ is preferably branched or straight-chain $C_3$–$C_{10}$-alkynylalkyl, in particular $C_3$–$C_6$-alkynylalkyl, such as 2-propynyl, 3-butynyl, 3-bityn-2-yl, 4-pentynyl, 1-pentyn-3-yl or 2-hexynyl, 2-propynyl, 3-butynyl and 3-butyn-2-yl being particularly preferred.

$R^5$ is preferably $C_1$–$C_5$-alkyl, such as methyl, ethyl, n-propyl, isopropyl, n-butyl, isobutyl, sec-butyl, tert-butyl or pentyl or the radicals stated under $R^4$.

The thiophene-2-carboxylic acid derivatives I can be prepared in a known manner by
(a) reacting an appropriately substituted thiophene carboxylic acid with an alcohol $R^4$OH when X is $OR^4$ or with a hydroxylamine $H_2N$—$OR^5$ when X is —NHOR$^5$ in the presence or absence of an acidic catalyst or dehydrating agent, or
(b) reacting an appropriately substituted thiophene-2carbonyl halide with an alcohol $R^4$OH when X is $OR^4$ or with a hydroxylamine $H_2N$—$OR^5$ when X is NHOR$^5$ in the
presence or absence of an acid acceptor.

The thiophene-2-carboxylic acids required as starting materials are known or can be prepared by generally known chemical processes (cf. Heterocyclic Compounds, Thiophene and its Derivatives, vol. 44, part 1, page 1 et seq., New York 1985, or U.S. Pat. No. 3,536,473). The thiophene carbonyl halides, of which the chlorides are particularly preferred, can be obtained from the corresponding carboxylic acids in a known manner, for example as described in Houben-Weyl, Methoden der organischen Chemie, page 463 et seq.

The alkynols $R^4$OH are known from the literature, are commercially available or can be prepared, for example as described in Houben-Weyl, Methoden der organischen Chemie, volume 6/1a, part 2, pages 1078–1090, 1980.

The acid can be esterified in a conventional manner, for example as described in Houben-Weyl, Methoden der organischen Chemie, volume VIII, page 516 et seq., Georg Thieme Verlag, Stuttgart 1952. For example, the reaction can be accelerated by adding a catalyst, such as sulfuric acid, hydrogen halide, sulfonic acid or an acidic ion exchanger, or the equilibrium of the esterification can be shifted in the desired direction by removing the reaction products from the reaction mixture, for example by removing the water by azeotropic distillation or adding a dehydrating agent, such as dicyclohexylcarbodiimide.

Starting from a thiophene-2-carbonyl halide, such as fluoride, chloride or bromide, the esterification can be carried out in the presence of an acid acceptor, as described in Houben-Weyl, loc. cit, page 543 et seq. Acid acceptors are conventional basic agents, in particular aliphatic, aromatic and heterocyclic amines, e.g. triethylamine, N,N-dimethylaniline, N,N-dimethylbenzylamine, pyridine, lutidine or 4-dimethylaminopyridine. Alkalimetalcarbonates, such as sodium carbonate or potassium carbonate, are also suitable acid acceptors.

The reaction can be carried out in a solvent or diluent. Some of the stated acid acceptors themselves or, for example, the following solvents or diluents or mixtures thereof are suitable for this purpose:

Aliphatic and aromatic hydrocarbons and chlorohydrocarbons, such as petroleum ether, benzene, toluene, xylene, gasoline, dichloromethane, chloroform, tetrachloromethane, 1,2-dichloromethane or chlorobenzene, ethers, such as diethyl and di-n-butyl ether, methyl tert-butyl ether, tetrahydrofuran or dioxane, ketones, for example acetone, methyl ethyl ketone or methyl isopropyl ketone, and nitriles, such as acetonitrile and propionitrile.

The starting materials are usually used in a stoichiometric ratio. Or, an excess of one or other of the starting materials may be quite advantageous in specific cases.

The novel thiophene carboxylates may furthermore be prepared by virtually all known processes of ester synthesis, for example by reacting corresponding carboxylic acid salts with propargyl halides, by transesterification reactions (cf. Houben-Weyl, loc. cit., pages 508–628; C. Ferri, Reaktionen der organischen Synthese, page 446 et seq., Georg-Thieme-Verlag, Stuttgart 1978; S. Patai, The Chemistry of Carboxylic Acids and Esters, page 505, Interscience Publishers, London 1969).

The amides can be prepared by aminolysis of thiophene-2carboxylic acids in a known manner, for example as described in Houben-Weyl, Methoden der organischen Chemie, volume E5, part 2, 4th edition, page 1144 et seq.

The aminolysis of more reactive carboxylic acid derivatives, such as acyl halides, e.g. acyl fluorides, chlorides or bromides, in the presence of the abovementioned acid acceptors is preferred (cf. loc. cit.).

The amines used for this purpose are known from the literature or are obtainable, for example, according to DE-A 36 15 473 or DE-A 36 31 071.

The thiophene-2-carboxylic acid derivatives of the formula I, and herbicidal agents containing them, may be applied for instance in the form of directly sprayable solutions, powders, suspensions including high-percentage aqueous, oily or other suspensions), dispersions, emulsions, oil dispersions, pastes, dusts, broadcasting agents, or granules by spraying. atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene isophorone, etc., and strongly polar solvents such as N,N-dimethylformamide, dimethy, sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids. e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90% by weight of active ingredient.

Examples of formulations are as follows:

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 3 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 5 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 11 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 30 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 28 is intimately mixed with 97 parts by weight of particulate kaolin. A dust is obtained containing 3% by weight of the active ingredient.

VII. 30 parts by weight of compound no. 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 30 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

IX. 40 parts by weight of compound no. 35 is dissolved in 60 parts by weight of a mixture consisting of 93 wt% of xylene and 7 wt% of the adduct of 8 moles of ethylene oxide to 1 mole of nonylphenol. A solution is obtained containing 40 wt% of the active ingredient.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants post-directed, lay-by treatment).

The application rates depend on the objective to be achieved, the time of the year, the plants to be combated and their growth stage, and are from 0.001 to 3.0, preferably 0.01 to 1.0, kg of active ingredient per hectare.

In view of the spectrum of weeds that can be controlled, the tolerance of the active ingredients by crop plants or the desired influence of the growth of the same, and in view of the numerous application methods possible, the compounds according to the invention may be used in a large number of crops. Those which follow are given by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. altissima | sugarbeets |
| *Beta vulgaris* spp. rapa | fodder beets |
| *Beta vulgaris* spp. esculenta | table beets, red beets |
| *Brassica napus* var. napus | rapeseed |
| *Brassica napus* var. napobrassica | swedes |
| *Brassica napus* var. rapa | turnips |
| *Brassica rapa* var. silvestris | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum*, *Gossypium herbaceum*, *Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (N. rustical) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. tuberosum | parsley |
| *Picea abies* | Norway spruce |
| *Abies alba* | fir trees |
| *Pinus* spp. | pine trees |
| *Pisum sativum* | English peas |

-continued

| Botanical name | Common name |
| --- | --- |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (s. vulgare) | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicla faba* | tick beans |
| *Vigna sinensis* (V. unguiculata) | cow peas |
| *Vitis vinifera* | grapes |
| *Zea mays* | Indian corn, sweet corn, maize |

To increase the spectrum of action and to achieve synergistic effects, the thiophene-2-carboxylic acid derivatives of the formula I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, (hetero)-aryloxyphenoxypropionic acid derivatives salts,. esters, amides, etc.

It may also be useful to apply the thiophene-2-carboxylic acid derivatives of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

The preparation of the active ingredients according to the invention is illustrated by the following examples.

EXAMPLE 1

4.5-Dibromothiophene-2-carboxylic acid-N-ethoxyamide

At room temperature, 6.8 g of 4.5-dibromothiophene-2-carboxylic chloride is stirred, in portions, into 6.8 g of O-ethylhydroxylamine hydrochloride in 10 ml of pyridine and 80 ml of tetrahydrofuran. After 30 minutes, dilute hydrochloric acid was added, and the product was filtered off and washed with water. Yield: 5.8 g; m.p.: 117–119° C.

EXAMPLE 2

4-Bromo-5-chloro-2-thiophenecarboxylic acid-(3-butynyl)-ester (a) 4-Bromo-5-chlorothiophene-2-carboxylic acid-(2'-hydroxyphenyl)-ester At room temperature, 55 g of 2,2-dichloro-1,3-benzodioxol is added to 50 g of 4-bromo-5-chlorothiophene in 200 ml of methylene chloride. While cooling with ice, 67.5 g of aluminum trichloride is added in portions. The whole is then stirred for 5 minutes at room temperature and refluxed for a further 5 minutes. Finally, it is poured into ice water, stirred and suction filtered. Working up in the usual manner gives 84 g of a crude crystalline product of melting point 145–147° C. and which is used in the next stage.

(b) 4-Bromo-5-chlorothiophene-2-carboxylic acid 80 g of the abovementioned compound is refluxed for 30 minutes in a 20% strength potassium hydroxide solution (800 ml). After the mixture has cooled, a precipitate is formed by adding concentrated hydrochloric acid. After suction filtration, the residue is again dissolved in water, while heating, by adding 20% strength potassium hydroxide solution. The pH is adjusted to approx. 10 by adding solid ammonium chloride. After suction filtration, the solid formed is discarded. The filtrate is acidified with concentrated hydrochloric acid, and the precipitate is filtered off and dried. Yield: 28.7 g; m.p.: >200° C.

(c) 4Bromo-5-chloro-2-thiophenecarboxylic chloride

The compound is synthesized in conventional manner from the carboxylic acid by reaction with thionyl chloride in toluene/n-pentane with catalytic amounts of dimethylformamide.

Reaction to the product of value (d) A spatula tip of 4-dimethylaminopyridine and 1.0 g of 3-butyn-1-ol are added to 3.0 g of the acid chloride prepared under (c) in 30 ml of tetrahydrofuran. Subsequently, 2.0 ml of triethylamine is dripped in and the mixture is stirred for 10 hours at room temperature. Conventional working up gives 2.8 g of the ester as an oil.

By employing other appropriate starting materials and amending the process conditions accordingly, the compounds listed below may be obtained.

TABLE 1

Thiophene-2-carboxylates I

| No. | $R^1$ | $R^2$ | $R^3$ | $R^4$ | Phys. Data/mp |
| --- | --- | --- | --- | --- | --- |
| 1 | Cl | Cl | H | $-CH_2-CH_2-C\equiv CH-$ | oil |
| 2 | $C_6H_5$ | Br | H | $-CH_2-C\equiv CH$ | |
| 3 | Br | Br | H | $-CH_2-CH_2-C\equiv CH$ | 50–53° C. |
| 4 | Br | Cl | H | $-CH_2-CH_2-C\equiv CH$ | oil |
| 5 | Cl | Br | H | $-CH_2CH_2-C\equiv CH$ | oil |

TABLE 1-continued

Thiophene-2-carboxylates

I

| No. | R¹ | R² | R³ | R⁴ | Phys. Data/mp |
|---|---|---|---|---|---|
| 6 | Cl | Br | H | —CH₂—C≡CH | |
| 7 | Cl | H | Cl | —CH₂—C≡CH | |
| 8 | Br | Br | H | —CH₂C≡CH | 60-64° C. |
| 9 | p-ClC₆H₄ | H | H | —CH₂C≡CH | |
| 10 | m-CF₃—C₆H₄ | H | H | —CH₂CH₂C≡CH | |
| 11 | Br | Br | H | —CH(CH₃)—C≡CH | 52-54° C. |
| 12 | Br | Br | H | —CH₂—CH₂—CH₂—C≡CH | |
| 13 | CF₃ | Br | H | —CH₂—C≡CH | |
| 14 | C₂H₅O | Br | Br | —CH₂C≡CH | |
| 15 | CF₃O | Br | H | —CH₂CH₂C≡CH | |
| 16 | n-C₄H₉ | Br | H | —CH₂C≡CH | |
| 17 | CH₃O | Br | Br | —CH(CH₃)—C≡CH | |
| 18 | p-F—C₆H₄ | Br | H | —CH(CH₃)—C≡CH | |
| 19 | I | H | H | —CH₂—CH₂—C≡CH | |
| 20 | F | Br | H | —CH(CH₃)—C≡CH | |
| 21 | NO₂ | H | H | —CH₂—C≡CH | |
| 22 | —CN | Br | H | —CH₂—C≡CH | |
| 23 | i-C₃H₇ | Br | H | —CH₂—C≡CH | |
| 24 | H | Br | Br | —CH₂—CH₂—C≡CH | |

TABLE 2

Thiophene-2-carboxamides

| No. | R¹ | R² | R³ | R⁵ | Phys. data/mp |
|---|---|---|---|---|---|
| 25 | Br | Br | H | C₂H₅ | 117-119° C. |
| 26 | Cl | Cl | G | —CH₂—C≡CH | |
| 27 | Cl | Br | H | C₂H₅ | 115-118° C. |
| 28 | p-Cl—C₆H₄ | Br | H | n-C₃H₇ | |
| 29 | Br | Cl | H | C₂H₅ | 125-126° C. |
| 30 | Cl | Cl | Cl | C₂H₅ | |
| 31 | Br | Br | H | —CH(CH₃)—C≡CH | |
| 32 | —CN | Br | H | C₂H₅ | |
| 33 | —NO₂ | H | H | —n-C₃H₇ | |
| 34 | m-CF₃—C₆H₄ | H | H | —n-C₃H₇ | |
| 35 | 3,5-Cl₂—C₆H₃ | H | H | C₂H₅ | |
| 36 | Cl | Cl | CH₃ | CH₃ | |
| 37 | Br | Br | H | CH₂CH₂—C≡CH | |

Use Examples

The herbicidal action of the thiophenes of the formula I on the growth of the test plants is illustrated in the following greenhouse experiments.

The vessels employed were plastic flowerpots having a volume of 300 cm$^3$ and filled with a sandy loam containing about 3.0% humus. The seeds of the test plants were sown separately, according to species.

For the postemergence treatment, either plants sown directly in the pots and grown there were used, or plants which were cultivated separately as seedlings and were transplanted to the vessels a few days before treatment.

Depending on growth form, the plants were grown to a height of 3 to 15 cm before being treated with the active ingredients, which were suspended or emulsified in water and sprayed through finely distributing nozzles. The application rate for postemergence treatment was 1.0 kg/ha.

The pots were set up in the greenhouse, species from warmer climates in warmer areas 20 to 35° C. and species from moderate climates at 10° to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the experiments were Amaranthus retroflexus ("AMARE"), Chenopodium album ("CHEAL")m Chrysanthemum corinarium ("CHYCO"), Helianthus annuus ("HELAN") and Oryza sativa ("ORYZA").

2.3-Dibromothiophene-5-carboxylic acid disclosed in U.S. Pat. No. 3,536,473 was used as comparative agent (A).

The compounds of Examples 3 and 8 from Table I, employed postemergence at a rate of 1.0 kg/ha, combated unwanted broadleaved plants very well and were tolerated by rice used as an example of a crop plant (Tables II and III).

TABLES I TO III

Control of unwanted broadleaved plants and tolerance by a crop plant on postemergence application of 1.0 kg/ha in the greenhouse:

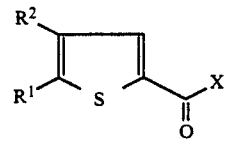

TABLE I

| Compound no. | R$_1$ | R$_2$ | X | Test plants and damage (%) | | |
|---|---|---|---|---|---|---|
| | | | | ORYZA | CHEAL | CHYCO |
| 3 | Br | Br | O(CH$_2$)$_2$C≡CH | 5 | 90 | 100 |
| A | Br | Br | OH | 0 | 60 | 0 |

TABLE II

| Compound no. | R$_1$ | R$_2$ | X | Test plants and damage (%) | | | | |
|---|---|---|---|---|---|---|---|---|
| | | | | ORYZA | CHEAL | HELAN | AMARE | CHYCO |
| 3 | Br | Br | O(CH$_2$)$_2$C≡CH | 5 | 100 | 100 | 100 | 100 |

TABLE III

| Compound no | R$_1$ | R$_2$ | X | Test plants and damage (%) | | | |
|---|---|---|---|---|---|---|---|
| | | | | ORYZA | CHEAL | AMARE | CHYCO |
| 8 | Br | Br | OCH$_2$C≡CH | 10 | 100 | 100 | 100 |

We claim:

1. A process for combating the growth of unwanted plants comprising treating unwanted plants and/or their habitat with a herbicidally effective amount of a thiophene-2-carboxylic acid derivative of the formula I

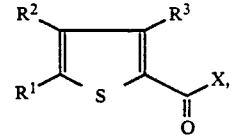

where

R$^1$, R$^2$ and R$^3$ are each hydrogen, halogen, branched or straight-chain C$_1$-C$_6$-alkyl, C$_1$-C$_8$-alkoxy, C$_1$-C$_6$-haloalkyl, C$_1$-C$_6$-haloalkoxy, nitro, cyano, unsubstituted phenyl or phenyl which is mono-to trisubstituted by C$_1$-C$_4$-alkyl, halogen, C$_1$-C$_5$-haloalkyl, C$_1$-C$_4$-alkoxy or C$_1$-C$_5$-haloalkoxy; and X is —OR$^4$ or —NH—OR$^5$, R$^4$ being branched or straight-chain C$_3$-C$_{10}$-alkynylalkyl which is unsubstituted or substituted by halogen, and being branched or straight-chain C$_1$-C$_5$-alkyl which is unsubstituted or substituted by halogen, or branched or straight-chain C$_3$-C$_{10}$-alkynylalkyl which is unsubstituted or substituted by halogen.

2. The process of claim 1, wherein the unwanted plants and/or their habitat are treated with a thiophene-2-carboxylic acid derivative in which X is —OR$^4$.

3. The process of claim 1, wherein the unwanted plants and/or their habitat are treated with a thiophene-2-carboxylic acid derivative in which X is —NH—OR$^5$.

* * * * *

UNITED STATES PATENT AND TRADEMARK OFFICE
CERTIFICATE OF CORRECTION

PATENT NO. : 5,034,049

DATED : Jul. 23, 1991

INVENTOR(S) : Reiner KOBER et al.

It is certified that error appears in the above-identified patent and that said Letters Patent is hereby corrected as shown below:

Claim 1, Col. 12, Line 52:

That part reading "being branched or straight-chain" should read -- $R_5$ being branched or straight-chain --

Signed and Sealed this

Seventeenth Day of November, 1992

*Attest:*

DOUGLAS B. COMER

*Attesting Officer*     *Acting Commissioner of Patents and Trademarks*